US005293772A

United States Patent [19]

Carr, Jr.

[11] Patent Number: 5,293,772

[45] Date of Patent: Mar. 15, 1994

[54] INSTRUMENTATION AND METHOD FOR EVALUATING PLATELET PERFORMANCE DURING CLOTTING AND DISSOLUTION OF BLOOD CLOTS AND FOR EVALUATING ERYTHROCYTE FLEXIBILITY

[75] Inventor: Marcus E. Carr, Jr., Richmond, Va.

[73] Assignee: Center for Innovative Technology, Herndon, Va.

[21] Appl. No.: 982,652

[22] Filed: Dec. 1, 1992

Related U.S. Application Data

[63] Continuation-in-part of Ser. No. 822,415, Jan. 17, 1992, Pat. No. 5,205,159.

[51] Int. Cl.[5] .......... G01N 33/48

[52] U.S. Cl. .......... 73/64.41; 73/790; 422/73

[58] Field of Search .......... 73/64.41, 760, 781, 73/788, 789, 790, 818; 422/73; 436/69

[56] References Cited

U.S. PATENT DOCUMENTS

| | | | |
|---|---|---|---|
| 4,317,363 | 3/1982 | Shen | 73/64.41 |
| 4,521,729 | 6/1985 | Kiesewetter et al. | 324/71.1 |
| 4,986,964 | 1/1991 | Carr, Jr. et al. | 73/64.41 |

OTHER PUBLICATIONS

Shifrin et al. "Measuring Transducer for Elastometric Medical Instruments", Biomed. Eng., vol. 14, No. 2, Nov. 1980.

*Primary Examiner*—Hezron E. Williams
*Assistant Examiner*—Michael Brock
*Attorney, Agent, or Firm*—Whitham & Marhoefer

[57] ABSTRACT

The performance of platelets can be best understood by monitoring both the force development and the elastic modulus of the blood clot during both clotting and dissolution of the blood clot. Intermittent application and removal of a compressive force on a blood sample (8) positioned between a pair of plates (12 and 14) throughout clot formation and dissolution provides a standard for using voltage output from a transducer (22) to determine force and elastic modulus parameters. Force development arises from the internal actions of the platelets during clot retraction. Elastic modulus provides a measure of the stiffness of the clot. Clotting can be measured as an increase in force development and clot elastic modulus. Clot dissolution can be determined by a dramatic decrease in force development and in elastic modulus. Providing the blood sample with a clot dissolving agent such as tPA allows determining the fibrinolytic potential of whole blood and, thus, aids in identifying patients at risk for thrombosis due to a decreased ability to dissolve clots. Clot elastic modulus provides a measure of erythrocyte flexibility.

10 Claims, 6 Drawing Sheets

INSTRUMENTATION AND METHOD FOR EVALUATING PLATELET PERFORMANCE DURING CLOTTING AND DISSOLUTION OF BLOOD CLOTS AND FOR EVALUATING ERYTHROCYTE FLEXIBILITY

CROSS-REFERENCE TO RELATED APPLICATIONS

This patent application is a continuation-in-part (CIP) patent application of the co-pending patent application entitled "Apparatus and Method for Measuring Clot Elastic Modulus and Force Development on the Same Blood Sample", filed Jan. 17, 1992, and having Ser. No. 07/822,415, now U.S. Pat. No. 5,205,159 to Carr, and that patent is herein incorporated by reference.

BACKGROUND OF THE INVENTION

1. Field of the Invention

This invention is generally related to blood analysis instrumentation and, more particularly, to instrumentation and techniques for monitoring the platelet function and clot structure of a blood sample during both clotting and dissolution of clots. In addition, the invention provides a new method of assessing erythrocyte flexibility.

2. Description of the Prior Art

U.S. Pat. No. 4,986,964 to Carr et al. discloses a clot retractometer which measures force development during platelet mediated clot retraction. This instrument has been shown to be a novel gauge of platelet function (see, Carr et al., Blood Coagulation and Fibrinolysis, 2:30-308 (1991), Carr et al., Am. J. of Med. Sci., 302:13-18 (1991), and Carr et al., Blood, 78:482A (1991)). However, clot retraction is dependent on intact platelet membrane structure, normal platelet metabolic function, fibrin structure and normal platelet-fibrin interactions. Changes in clot retraction are sensitive to a spectrum of both fluid phase and platelet abnormalities. Force development is completely dependent on platelet function and if platelet function is abnormal or if no platelets are present, force development will be completely absent.

When tissue injury occurs, bleeding is halted and vascular integrity is restored by activation of the hemostatic mechanism. A complex combination of blood protein interactions and cellular activations leads first to the formation of a platelet plug and subsequently to the production of the fibrin-platelet clot. Since the amount of blood loss is directly proportional to the time required to stop the bleeding, both sets of reactions occur rapidly. While the ability to stop injury-induced blood loss is critical, the capability of turning flowing blood into a solid is a source of serious problems. Clot formation within a vessel leads to decreased flow, ischemic damage and, if the clot is not removed, eventual tissue infarction.

To avoid clot formation in non-injured tissue and to prevent clot propagation from the site of injury to other locations within the vascular bed, the coagulation system is balanced by a series of potent inhibitors. Furthermore, the clot itself is designed as a temporary patch. Once bleeding stops and tissue repair is initiated, the clot is dissolved by the enzyme plasmin.

Under normal conditions, the coagulation system remains in a fine balance. Pathologic alterations of the system may induce a risk of hemorrhage or increase the potential for thrombosis. An example of the former would be the bleeding disorder of hemophilia which results from a low level of Factor VIII, a blood clotting protein. An example of the latter would be recurrent venous thrombosis in individuals who have decreased levels of the coagulation inhibitor antithrombin III. Patients with decreased ability to remove clots, decreased fibrinolytic potential, are also at risk for thrombosis.

Currently, the evaluation of patients for increased risk of bleeding is accomplished through a series of coagulation screening tests. The prothrombin time (PT) and partial thromboplastin time (PTT) identify patients at risk for bleeding and direct the clinician to more specific tests to define the cause of the increased risk. If the PT is prolonged (i.e. takes longer to clot than normal plasma), the patient is at increased risk for bleeding. Since prolongations of the PT are known to occur in specific factor deficiencies, the appropriate factor levels can be measured to define the abnormality. Unfortunately, screening tests for fibrinolytic potential are presently not available. Furthermore, tests which identify patients at risk for thrombosis due to decreased ability to dissolve clots have not been reported and are not in use.

Clot dissolution can be monitored using clot optical density measurements or by measurement of radioactive material release from the clot. The optical density technique relies on the fact that clot formation increases the turbidity of the plasma sample while clot dissolution reduces turbidity back to baseline, pre-clot values (see, Carr et al., Thromb. Haemostas., 67:106-110 (1992)). In this technique, clotting is monitored as a rise in turbidity, while clot dissolution is seen as a fall in clot turbidity. The radioactive tracer technique involves the addition of radiolabelled clotting protein, for example $^{125}$I labelled fibrinogen, to the patient sample (see, Carr et al., Thromb. Haemostas., 67:106-110 (1992) and Knight et al., Thromb. Haemostas., 46:593-596 (1981)). As clotting occurs, the labelled fibrinogen is incorporated into the clot structure. During subsequent clot dissolution, radioactive fragments are released. The rate of radioactivity release is proportional to the rate of clot dissolution.

A major problem with the turbidity technique is that it cannot be utilized in systems containing erythrocytes. A major problem with the tagged fibrinogen technique is the necessity for using radioactive material. Moreover, a divergence in results has been observed with the two techniques. When dissolution is rapid, both techniques yield comparable dissolution times. However, when dissolution is delayed, dissolution times measured by the turbidity technique tend to be longer than those measured by $^{125}$I release (see, Carr et al., Thromb. Haemostas., 67:106-110 (1992)).

Altered erythrocyte deformability is thought to play a role in multiple disease processes. Unfortunately, measurement of erythrocyte flexibility remains somewhat problematic. Currently, the majority of investigators have utilized erythrocyte filtration techniques to measure flexibility. The common feature of these methods is the flowing of erythrocytes through filters which typically have pores of uniform size. Erythrocytes either flow through under low pressure (e.g., a static column of blood), or are forced through at higher pressures. Results are reported as a "filtration index". Filtration techniques have several major deficiencies. First, they are difficult to reproduce. Results vary from laboratory to laboratory, and may vary over time in the same laboratory. Second, they fail to take into account the possibility that microvascular channels may be flexible. Third, they ignore possible contributions of the clotting system. Another prior method of measuring erythrocyte flexibility is called ektocytometry. This method involves the deformation of cells in shear fields with simultaneous monitoring of shape change. Ektocytometry has the advantage of being a non-flow method of monitoring erythrocyte flexibility; however, it is indirect, expensive, and not widely available. In view of the above, it would be advantageous to have an inexpensive and reproducible method of evaluating erythrocyte flexibility.

SUMMARY OF THE INVENTION

It is an object of this invention to provide a superior method of monitoring clot destruction than the turbidity and radiolabelling techniques described in the prior art.

It is another object of this invention to provide instrumentation and a method for obtaining quantitative measurements of both clot structure development and clot dissolution on the same blood sample.

It is another object of this invention to provide instrumentation and a method for assessing erythrocyte flexibility.

According to the invention, simultaneous measurements of force development and clot elastic modulus are performed on a blood sample. These measurements are used to identify clot formation and dissolution, as well as to assess erythrocyte flexibility. Experiments utilizing an agent which induces fibrinolysis shows that clot destruction can be readily identified from a dramatic drop in force development (clot retraction) and a dramatic decrease in clot elastic modulus. Experiments conducted using normal and sickled erythrocytes shows a measurable effect on clot elastic modulus.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
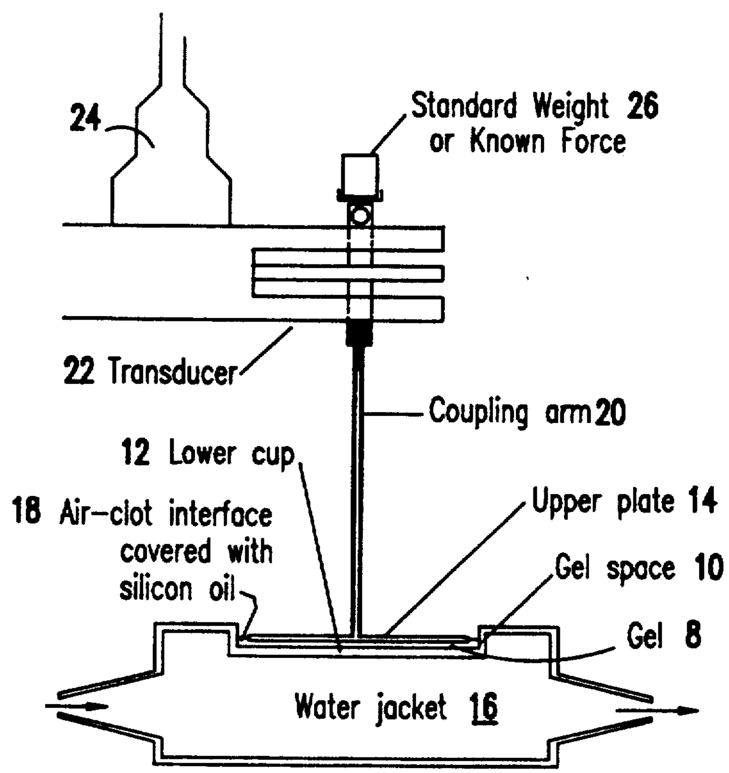
FIG. 1 is an enlarged view of the sensor arrangement described in U.S. Pat. No. 5,205,159 to Carr.
Figure 2:
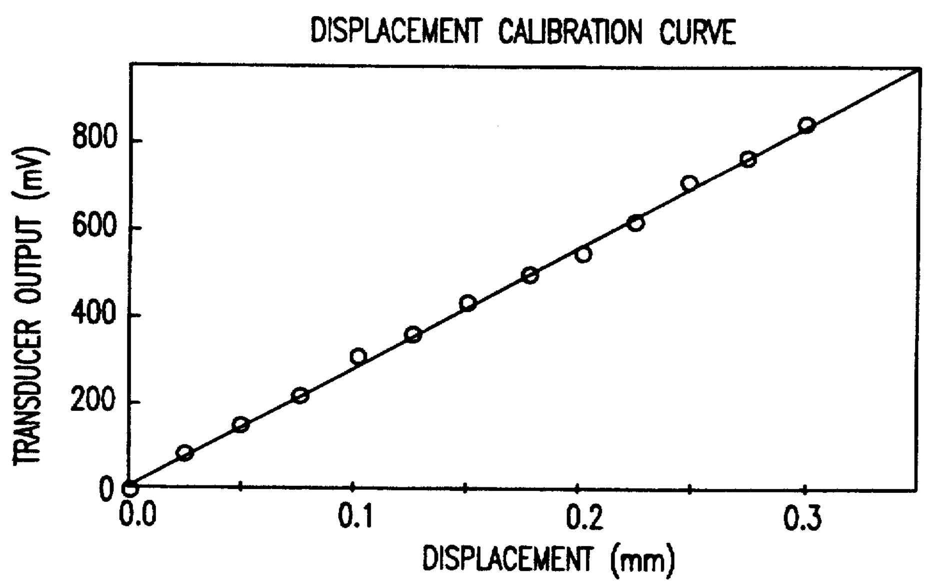
FIG. 2 is a graph of a force calibration curve where voltage output from a transducer is plotted versus displacement of a plate.

U.S. Pat. No. 5,205,159 to Carr describes instrumentation which allows monitoring both clot retraction and clot elastic modulus development during clot formation. FIGS. 1 and 2 are taken from that patent.

FIG. 1 shows a blood sample (gel) 8 positioned in gel space 10 between a thermostated lower cup 12 and upper plate 14. The blood sample 8 can be whole blood, plasma, platelet rich plasma (PRP) or platelet poor plasma (PPP), etc. Several different elements can be used for thermostatic control. FIG. 1 shows only one example wherein fluid flowing through a water jacket 16 maintains the temperature of the blood sample 8. As explained in U.S. Pat. No. 4,986,964 to Carr et al. and U.S. Pat. No. 5,205,159 to Carr, maintaining the temperature at or around body temperature (35°–38° C.) and controlling the microenvironment of the blood sample yields reproducible results for clot retraction measurements. The preferred microenvironmental conditions for the blood sample 8 are approximately pH 7.4, ionic strength of approximately 1.0 to 2.0, and calcium ion concentration of 5 mM to 10 mM. To prevent evaporation of the blood sample 8 during a measurement cycle, the air-clot interface 18 between the upper plate 14 and lower cup 12 should be covered with silicone oil or some other suitable material.

As described in both U.S. Pat. No. 4,986,964 to Carr et al. and U.S. Pat. No. 5,205,159 to Carr, platelets within the blood sample 8 adhere to the bottom of the cup 10 and plate 14, and pull downward during clot retraction. A coupling arm 20 connects the upper plate 14 to a transducer 22. Movement of the plate 14 towards the cup 10 under the influence of clot retraction exerts a strain on the transducer 22 which outputs a voltage which is proportional to the force exerted by the platelets during clot retraction. This voltage can be sent by wire connections 24 to an amplifier and the amplified signals can be plotted on a plotter or output on a cathode ray tube (CRT).

FIG. 2 shows that there is a linear relationship between the displacement of the upper plate 14 towards the lower cup 12 and the transducer 22 output. The slope of the line in FIG. 2 serves as a displacement calibration constant ($C_d$), whereby voltages developed during clot retraction can be converted directly to force measurements by multiplying them by the force calibration constant.

As is particularly discussed in U.S. Pat. No. 5,205,159 to Carr, by applying a known amount of force to the upper plate 14, which can be by application of weight 26 or by other means, the blood sample 8 between the upper plate 16 and lower cup 12 can be compressed. The degree of deflection of the upper plate 14 towards the lower cup 12 caused by the application of the force is sensed by the transducer 22 which provides a voltage output. With the knowledge of the amount of force applied and by detecting the degree of displacement of the upper plate 14 towards the lower cup 12 under the influence of the applied force, the elastic modulus of the blood sample can be calculated. Therefore, a particular advantage of the instrumentation described in U.S. Pat. No. 5,205,159 Carr is that both the clot elastic modulus and force development can be determined for a single blood sample.

One aspect of this invention is particularly concerned with using the instrumentation described in U.S. Pat. No. 5,205,159 to Carr in a new way to monitor clot elastic modulus (a measure of clot structure) and force development (a measure of platelet function) during both clot formation and clot dissolution. The data generated are both quantitative and physically well defined. Force is measured in dynes, and elastic modulus is reported in dynes/cm$^2$. Measurements can be made on samples of whole blood, plasma, platelet poor plasma (PPP), or platelet rich plasma (PRP), etc.

For exemplary purposes, the following method and data analysis illustrate the utility of this invention in monitoring clot elastic modulus and force development during clotting and dissolution.

METHOD 1

Patient blood is obtained by venipuncture and is collected in sodium citrate (0.38%) which serves as an anticoagulant. Two milliliters (mls) of blood sample 8 (e.g., whole blood) is placed in the thermostated sample cup (12 on FIG. 1) of the instrumentation described in U.S. Pat. No. 5,205,159 to Carr. At time zero, human α-thrombin (1 NIHu/ml), which is a clotting agent, and human tissue plasminogen activator (tPA) (50 IU/ml), which is a clot dissolving agent, are simultaneously added to the blood sample 8. Other clotting agents and clot dissolving agents might also be used within the practice of this invention including tissue thromboplastin, Russel Viper Venom, Reptilase, batroxobin (as well as other snake venom enzymes) as clotting agents, and including prourokinase, urokinase, streptokinase (as well as its modified species, e.g., acetylated forms, etc.) as fibrinolytic agents (clot dissolving). The upper plate 14 is lowered into position. Silicone oil is layered on the exposed blood-air interface 18. Signals from the transducer 22 are recorded throughout clotting and dissolution.

Every thirty seconds, a downward force is applied to the forming clot. In a preferred operation, the force remains in place for 15 seconds, is removed for 15 seconds, and then the cycle repeats. The application of the force produces small downward displacements of the upper plate 14. Deflection of the upper plate 14 towards the lower cup produces a voltage potential which is recorded on an X-Y plotter. The magnitude of the voltage is directly and linearly proportional to the amount of displacement of the upper plate 14.

As clotting proceeds, the structure becomes more rigid and the amount of displacement for a given force decreases. Structural rigidity or integrity can be quantified as the clot elastic modulus. The modulus is simply the ratio of stress applied to strain produced. In this case, the stress is the force applied, and the strain is the amount of deflection of the upper plate 14. Both parameters are known and the elastic modulus is calculated for each voltage spike.

The tPA added to the blood sample 8 at time zero, cleaves the pro-enzyme plasminogen to its active form plasmin (see, Lijnen, Semin Thromb Hemostas, 8:2-10 (1982)). Other clot dissolving agents would have a similar effect. This activation process is greatly enhanced in the presence of fibrin which forms during clotting. Once activated, plasmin cleaves fibrin at multiple sites (see, Francis, J. Clin. Inves., 66:1033-1043 (1980) and Marder, Ann NY Acad. Sci., 408:397-406 (1983)). As fibrin fibers are partially cut at multiple points along their length, the structural integrity of the network (clot) is increasingly compromised and the clot elastic modulus declines. At some point, the clot simply falls apart, the elastic modulus falls to zero and deflections produced by the applied force return to their pre-clot value. The time at which the elastic modulus falls to baseline can be defined as the "tCLT" for "tPA-induced clot lysis time".

DATA ANALYSIS 1

Figure 3:
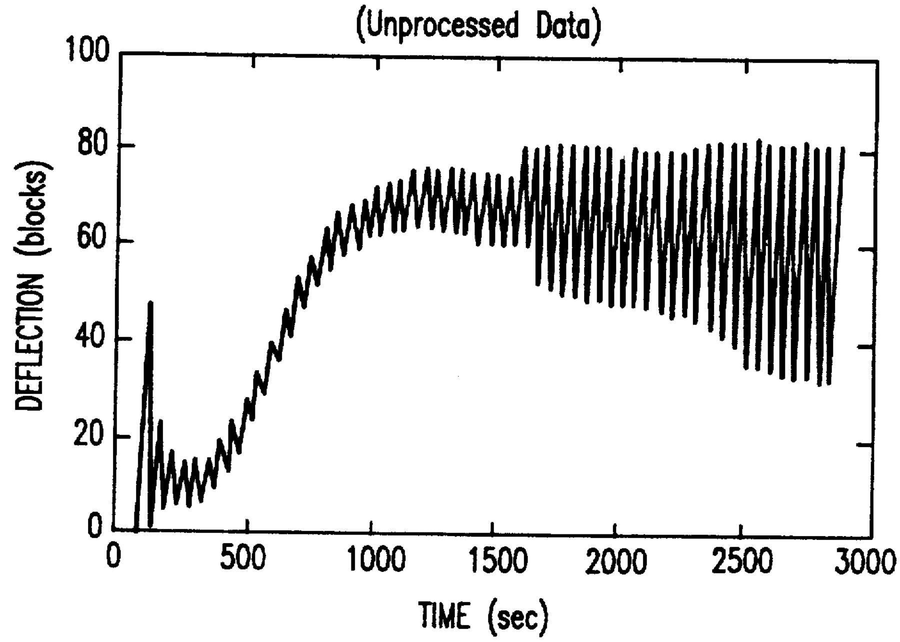
FIG. 3 is a graph showing raw data obtained using the instrument described in U.S. Pat. No. 5,205,159 where the weight is applied intermittently during both clot formation and dissolution and x-y plotter pen deflection is detected with respect to time.

FIG. 3 is an example of raw data obtained when a force is applied intermittently to the upper plate as a clot forms and is dissolved as described in the method discussed above. In this case, citrated whole blood was clotted with thrombin (lu/ml) and calcium (10 mM) which were added at time equal zero. Tissue plasminogen activator (tPA) was also added at time zero to induce subsequent clot dissolution. Upward deflections of the curve represent force transmission to the transducer. The overall gradual rise and subsequent fall of the curve is due to forces generated within the clot. The spikes super-imposed on the smooth curve are the result of external forces applied to the clot. Specifically, the spikes result from the intermittent application of the weight or other known amount of force to the upper plate.

Figure 4:
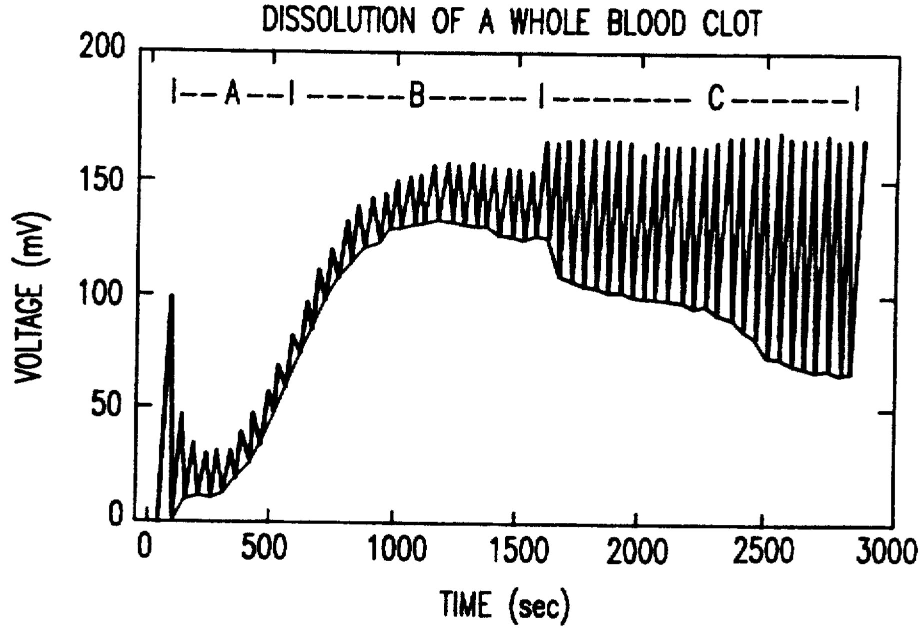
FIG. 4 is a graph showing processed data from FIG. 3 where a voltage output is plotted with respect to time, wherein a spiking upper curve reflects the application of the externally applied force and a smooth lower curve reflects the internal forces developed from within the clot.

FIG. 4 shows a plot of the voltage output with respect to time which is derived from the raw data shown in FIG. 3. As set forth in Equation 1, the deflection of the x-y plotter shown in FIG. 3 is converted to voltage based on the gain constant of the plotter.

$$(\text{Voltage}) = (\text{Deflection}) \times (\text{gain Constant}) \quad (1)$$

In the case illustrated in FIG. 3, each block was equal to 2 mV and a simple conversion yields the spiking upper curve displayed in FIG. 4.

Also shown on FIG. 4 is a smooth lower curve that reflects the forces originating from within the clot. In contrast, the spiking upper curve is produced by external forces (e.g., the intermittently applied weight). With reference to the smooth lower curve, it can be observed that there is a short lag period followed by a steep upward deflection, a subsequent plateau, and finally a gradual decline.

The data in the smooth lower curve can be converted to true force measurements utilizing concurrent information from the "spiking" data of the upper curve. Each spike represents the amount of voltage generated by a known force. Since the transducer output is linear with respect to force, the ratio of output voltage to force provides a constant for converting the data in FIG. 4 into force measurements shown in FIG. 5. This technique is a significant improvement over the technique described in U.S. Pat. No. 5,205,159 to Carr. The previous Carr technique approximated force based on the final clot structure. In contrast, this technique measures the clot structure at each time point. This information allows the "true" force to be calculated. The previous Carr technique assumed the final elastic modulus existed throughout the measurement. This is obviously not the case. Thus, the previous Carr technique tended to overestimate early force development. As clot formation approaches completion, both techniques yield the same results.

Figure 5:
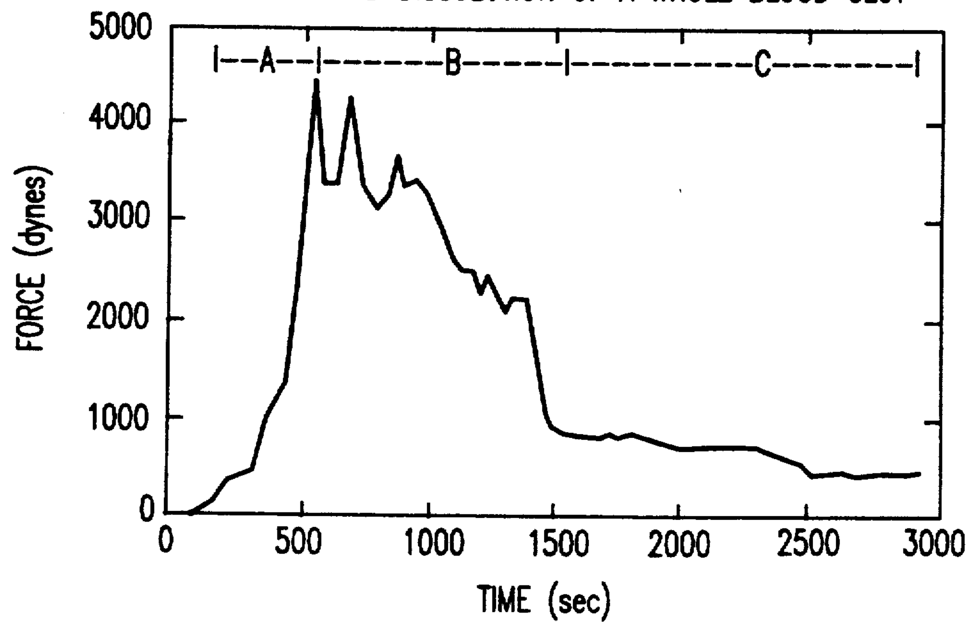
FIG. 5 is a graph which plots force versus time throughout clot formation and dissolution.

FIG. 5 shows that the blood sample undergoes a short lag phase followed by rapid force development.

However, unlike the voltage data shown in FIG. 4, FIG. 5 reveals that force transmission does not plateau. Following a period of gradual decline (600 to 1600 seconds), force transmission drops precipitously to near baseline values. The lag phase corresponds to the time required for fibrin assembly, platelet attachment and generation of a network of adequate mechanical resilience to allow transmission of forces to the upper plate. The rapid upward spike (time period A) is due to forces generated by platelets during clot retraction where the platelets exert a pulling force on the upper plate towards the lower cup. The gradual decline in force beginning at 600 seconds (time period B) results from a gradual weakening of the clot network during early plasmin mediated fibrinolysis. At approximately 1600 seconds, total network collapse occurs, resulting in a catastrophic fall in force transmission (time period C).

The ratio of applied force to induced material deformation is the elastic modulus of a material. Materials which resist deformation have a high elastic modulus. In this process, a known force (STRESS) is applied to the upper surface of the clot, and the amount of deformation (STRAIN) is measured. Equation 2 shows the elastic modulus is simply the ratio of STRESS to STRAIN:

$$\text{Elastic Modulus (EM)} = \text{STRESS/STRAIN} \quad (2)$$

Stress is typically defined as force per unit area (Equation 3):

$$\text{Stress} = \text{Applied Force/Area Applied} \quad (3)$$

In the present case, the force applied is a standard weight of known mass (m), (g) is the gravitational force constant, and the area of application is simply the area of the upper plate 14. Since the upper plate is circular with a radius of (r), the stress is simply indicated by Equation 4:

$$\text{Stress} = (mg)/\pi r^2 \quad (4)$$

Strain is the degree of shape change induced by the applied force. In the present case, the initial gel dimension (L) in the axis of the applied force is simply the distance between the cup 12 and the plate 14. The amount of deformation is simply the distance moved (s) by the upper plate 14 when the force is applied. Hence, Equation 5 shows that strain can be calculated as follows:

$$\text{Strain} = s / L \quad (5)$$

Thus, elastic modulus can be quickly calculated using either Equations 6 or 7.

$$\text{Elastic Modulus} = [(mg)/(\pi r^2)]/(s/L) \quad (6)$$

$$\text{Elastic Modulus} = [g/(\pi r^2)]*[mL/s] \quad (7)$$

where g equals 980 $cm/sec^2$ and $\pi$ equals 3.14159. The other constants are a function of the instrumentation employed. For example, the radius r of the upper plate can be 1 or more centimeters (good results have been obtained when r=1.75 cm), m is simply the mass of the applied weight and can be 2 gm, 5 gm, etc., L is the gap between the cup 12 and plate 14 and is typically set on the order of millimeters (good results have been obtained when L=2 mm), and s is the deflection distance of the upper plate 14 towards the cup 12. As explained above, since the transducer 22 is a displacement transducer, the voltage generated by the transducer is a linear function of the distance (deflection) moved by the upper plate 14 towards the lower cup 12.

Equation 8 relates the voltage output to the distance moved (s) by the upper plate.

$$\text{Voltage} = s / C_d \quad (8)$$

$C_d$ is a displacement calibration constant (see FIG. 2 above where $C_d$ is the inverse slope of the line in FIG. 2) which relates the displacement of the plate 14 to the voltage output of the transducer. As is explained in U.S. Pat. No. 5,205,159 to Carr, the curve shown in FIG. 2 can be generated by moving the plate a known distance towards the cup and detecting the voltage output of the transducer. The slope of the curve which results yields the force calibration constant $C_d$. In the instrument used in the experiments described above, $C_d$ was equal to $3.85*10^{-4}$ mm/mV. Thus, Equations 9 and 10 can be used to calculate Elastic Modulus (EM).

$$EM = [(g)/(\pi r^2)][(ml)/(VC_d)] \quad (9)$$

$$EM = [(gml)/(\pi r^2)](1/V) \quad (10)$$

Figure 6:
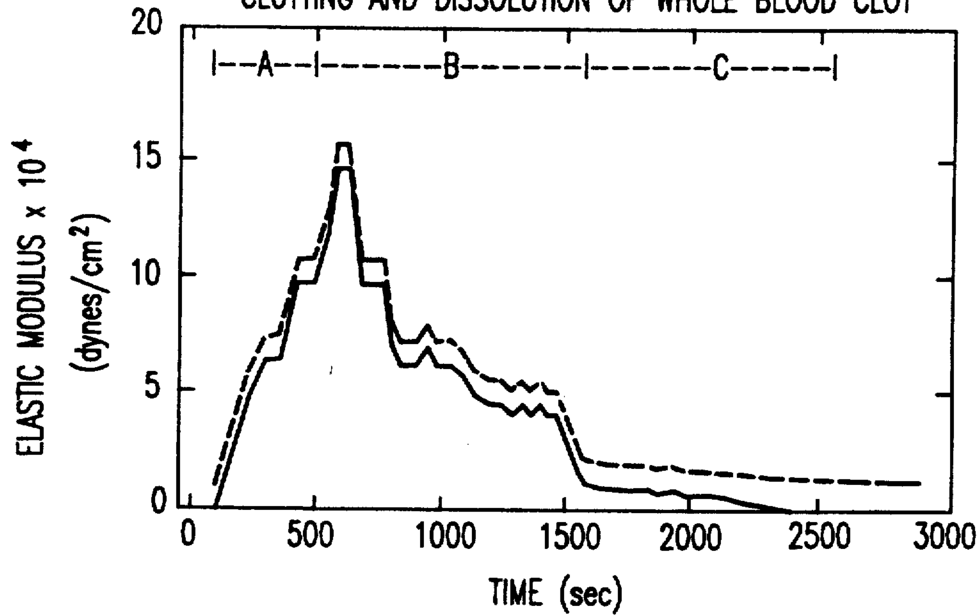
FIG. 6 is a graph which plots elastic modulus versus time throughout clot formation and dissolution.

FIG. 6 shows elastic modulus versus time for the blood sample throughout the clotting and dissolution phases, where the elastic modulus was calculated using the above equations and the voltage and force data provided in FIGS. 4 and 5. There are two problems with the calculation scheme discussed above for which adjustment is needed. First, the transducer itself has elastic properties. Second, unclotted fluid in the sample cup exerts a buoyant force on the upper plate. Thus, even in the absence of a clot, a substantial elastic modulus is measured. This problem is avoided by arbitrarily assigning a value of zero to the initial elastic modulus measurement. This is entirely reasonable since the elastic modulus of water is zero. "Re-zeroing" the system at the beginning of the measurement effectively counterbalances the influences of the inherent elastic properties of the apparatus. Hence, the excess elastic modulus generated during clotting and subsequent events is measured after "rezeroing". The effect of re-zeroing the system is seen as a shift between the solid and broke lines in FIG. 6.

Figure 7:
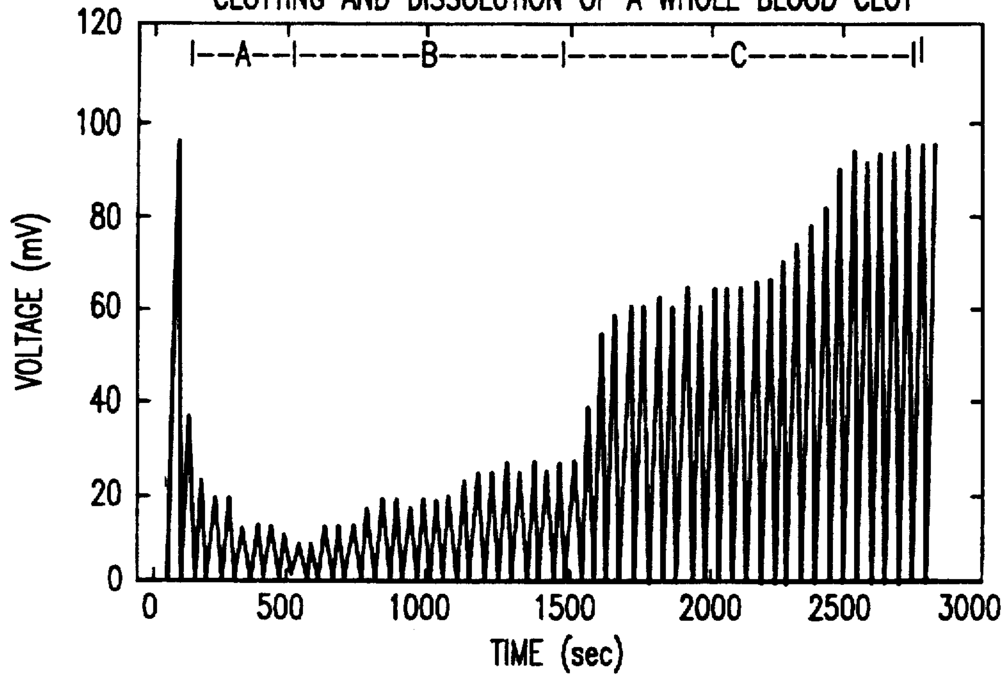
FIG. 7 is a graph which plots the change in voltage for the applied force with respect to time.

FIG. 7 shows another means by which the clot dissolution can be easily identified. Specifically, the effect of fibrinolysis on clot structure is easily appreciated by examining changes in spiking data versus time. Each spike represents the amount of downward deflection of the upper plate when a standard force is applied. The force applied is the same for each spike. During time period A, fibrin network formation proceeds and the gel's mechanical strength increases. As a consequence, the gel's resistance to deformation increases and the amount of deflection of the upper plate declines. This is easily appreciated in FIG. 7 where the lower point of the spike data has been normalized to zero. During time period B, the fibrin network is gradually weakened by plasmin induced fiber strand breaks. This is seen as a gradual increase in the amount of deflection versus time. At approximately 1600 seconds, network collapse begins to occur and resistance to deformation rapidly declines with the return of deflection values back to pre-clot levels.

A particular advantage of the present technique is that the force development and elastic modulus of a single blood sample can be determined throughout the stages of both blood clotting and clot dissolution. Thus, the instrumentation and analysis technique of this invention allows a single sample of whole blood (or plasma) to be used to provide information about clotting time (lag phase), platelet function (force development), and adequacy of clot structure (elastic modulus). As discussed above, the "true" force is calculated by periodically applying a weight to the blood sample throughout the clotting cycle. This periodic application of the weight and calculation cycle takes account of the fact that the elastic modulus of the blood sample changes during clotting. Hence, force development during early stages of clotting are more accurately determined.

Another particular advantage of the present technique is that the fibrinolytic potential of a patient's blood can be easily identified. Specifically, by providing the blood sample with tPa, the time period for clot dissolution can be determined. By comparing the time for clot dissolution with the response determined for normal blood samples, patients at risk for thrombosis due to a decreased ability to dissolve clots can be identified and treated. Other clot dissolving agents might also be used. All that would be required would be to determine a standard dissolution time for normal blood, so that when the dissolution time for a sample under test strays beyond a normal period, the patient's blood can be identified as having reduced fibrinolytic potential. This measurement has not been available for whole blood prior to the development of this instrument and analysis technique.

Another aspect of this invention is concerned with the measurement of erythrocyte deformability or flexibility. Erythrocyte flexibility is an important parameter in disease such as sickle cell disease.

There is increasing evidence that the coagulation system is activated in sickle cell disease. Markers of platelet activation, such as platelet factor 4 and beta-thromboglobulin, are elevated. Fibrinogen level is elevated in stable state sickle cell disease and is increased even higher during vaso-occlusive crisis. Markers of thrombin activation, such as prothrombin fragment II, and fibrin generation, such as fibrinopeptide A, are elevated in sickle cell disease. D-dimer levels, indicating deposition and subsequent dissolution of crosslinked fibrin, are routinely elevated in sickle cell disease and show a peak during vaso-occlusive crisis. While levels of some coagulant proteins are elevated, natural anticoagulant levels, including ATIII, protein C and protein S are decreased in sickle cell disease. Finally, the plasma of sickle cell disease contains prothrombic spicules originating from the membrane of SS erythrocytes. These spicules, with altered phospholipid conformation, have been shown to enhance clotting in assays such as the Russell Viper venom test. In summary, sickle cell disease is a state characterized by circulating procoagulants, elevation of certain clotting factors, depression of natural anticoagulants, and laboratory evidence of both platelet and fluid phase coagulant activation. Whether and active pathogenic component of simple epiphenomenon, activation of hemostatic process occurs in sickle cell disease.

The role of clotting in vaso-occlusive clotting events remains to be defined. Based on the laboratory findings presented above, some investigators classify sickle cell disease as a state of chronic DIC. If clotting is a component of the microvascular process involved with vaso-occlusive crisis, interactions of fibrin and erythrocytes may be important. Decreased or absent blood flow due to sludging of erythrocytes must further raise the risk of thrombosis in involved vessels. Clots formed in the microcirculation must certainly contain erythrocytes. In sickle cell disease, these clots may contain a combination of reversibly and irreversibly sickled cells. It has been demonstrated that normal erythrocytes will flow out of macroscopic clots. The phenomenon of erythrocyte washout is due to the large, inherent pore size of fibrin gels and to the remarkable deformability of the normal erythrocytes. Most recently, it was demonstrated that there is decreased bulk flow through and decreased red cell washout from clots containing sickled erythrocytes.

The long term objective in sickle cell disease is to reduce significant associated morbidity and mortality. If intermittent vascular occlusion did not occur in sickle cell disease, this goal would be accomplished. Since SS hemoglobin containing cells exhibit altered shape and decreased ability to pass through nondeformable pores, a primary goal of current research is to develop ways of enhancing the deformability of SS hemoglobin containing erythrocytes.

An investigation using the instrumentation of FIG. 1 was conducted to study the effects of erythrocytes on clot elastic modulus. Clot elastic modulus was measured according to the procedures described above. As shown below, by comparing the elastic modulus of clots containing red cells to similar clots formed in the absence of red cells, the relative contribution of erythrocytes to clot elastic modulus can be assessed. In addition, this study compared the relative effects of normal and sickled erythrocytes on clot elastic modulus. As shown below, less flexible, sickled erythrocytes have a greatly increased elastic modulus when compared to normal erythrocytes. The effect of poloxamer 188, a rheologic agent, on sickle cell flexibility was also investigated, and it is shown below that this agent can significantly increase sickle cell flexibility. The investigation and results presented below are for exemplary purposes only, and do not limit the scope of the invention in any way.

METHOD 2

Human thrombin, greater than 90% alpha, was purchased as lyophilized powder from Sigma Chemical Company. The material with a specific activity of 4300 NIH units/ml was dissolved in water, diluted with 0.10M NaCl to a final concentration of 20 units/mL, divided into 1 mL lots, and frozen at −90° C. Thrombin was free of plasmin and plasminogen. Nanopure water was used in the preparation of all solutions.

Human blood was obtained in citrated glass tubes by sterile venipuncture of normal volunteers. PPP was prepared by spinning at low speed to remove large formed elements and then respinning at 20,000 g for twenty minutes to remove platelets. PPP was pooled, maintained at room temperature, and utilized within four hours. The buffy coat was carefully removed from the surface of the packed erythrocytes and the red cells were maintained at room temperature. The fibrinogen concentration of plasma samples was determined by a modified method of Clauss, Acta. Haematol., 17:237 (1957).

Blood containing hemoglobin SS bearing cells was obtained via venipuncture from volunteers with documented sickle cell disease. PPP and packed erythrocytes were prepared as outlined above. The packed erythrocytes were treated with sodium metabisulfite by mixing equal volumes of red cells and 3% sodium metabisulfite. The mixture was covered and incubated at room temperature for one hour. Sickling of the cells was confirmed by microscopic examination of the blood. The percentage of sickled cells, typically >90%, was determined by counting 200 cells. The mixture of cells and sodium metabisulfite was subsequently centrifuged at 2,000 g for five minutes and the sodium metabisulfite containing supernatant was removed.

Elasticity measurements were made by placing PPP, PRP or whole blood in the thermostated sample cup (e.g., gel space 10 in FIG. 1) of the clot retractometer. At time zero, human $\pi$-thrombin (1 NIH unit/ml) was added. The upper plate 14 was lowered into position, silicone oil was layered on the exposed blood-air interface 18, and the measurement was initiated. Every thirty seconds a downward forced was applied to the forming clot. This force remained in place for fifteen seconds, was removed for fifteen seconds, and the cycle repeated. The application of the force produced small downward displacements of the upper plate. These deflections generated a voltage potential which was recorded on an X-Y plotter. As discussed in detail above, the magnitude of the voltage was directly and linearly proportional to the amount of displacement. As clotting continued, the structure became more rigid and the mount of displacement for a given force decreased. Structural rigidity or integrity was quantified as the clot elastic modulus.

DATA ANALYSIS 2

Figure 8A:
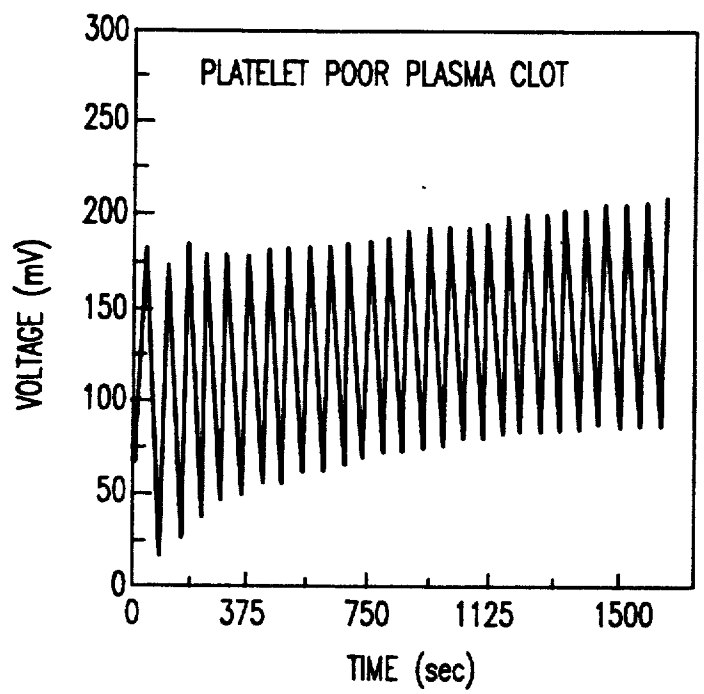
FIGS. 8*a–c* are graphs showing the elastic modulus development during clotting for platelet poor plasma (PPP), platelet rich plasma (PRP), and whole blood, respectively.
Figure 8B:
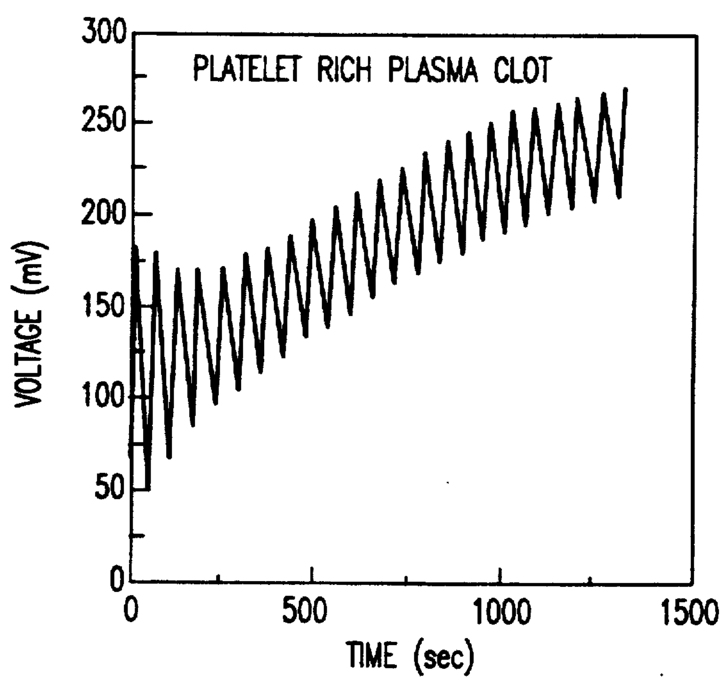
Figure 8C:
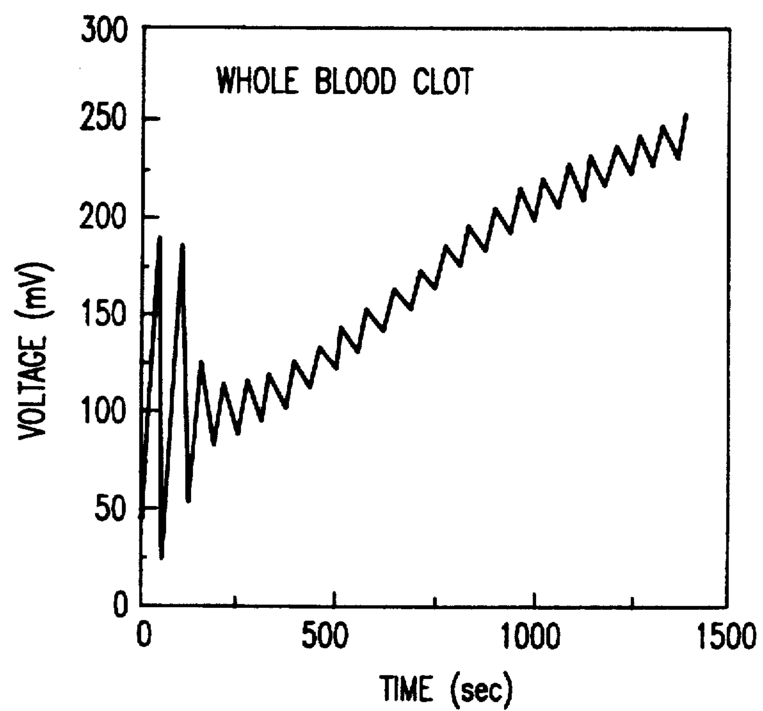

FIGS. 8*a–c* demonstrate the impact of cellular elements on clot formation and structure. FIG. 8*a* shows the clot formation in PPP. Thrombin (1 NIH u/ml) and calcium (10 mM) were added to citrated PPP at time zero. Other clotting conditions included: temperature 37° C., pH 7.4, and ionic strength 0.15. Since fibrin structure also affects clot modulus, factors which alter fibrin formation (e.g., ionic strength, calcium concentration, pH) need to be strictly controlled. The voltage spikes are produced by repetitively placing a known downward force on the clot. Each voltage spike yields one elastic modulus measurement. The deflections decline in amplitude as the clot develops increased structural resilience, i.e., increased elastic modulus. The minimal gradual upswing in baseline voltage is caused by weak clot retraction forces that result from residual platelet contamination. FIG. 8*b* presents data obtained during clotting of PRP. The gradual upward swing of the curve is due to platelet mediated force development during clot retraction. The height of each voltage spike is inversely proportional to the elastic modulus. When compared to FIG. 8*c*, the voltage spikes caused by the external force are seen to be smaller. Thus clots formed in the presence of platelets have higher elastic properties. FIG. 8*c* presents data obtained during clotting of whole blood (hematocrit was approximately 40%) and demonstrates the effect of erythrocytes on clot elastic modulus. The effect is rather profound, with at least a doubling of elastic modulus.

The effects of erythrocytes on clot elastic modulus in the absence of platelets was evaluated by forming clots from a mixture of packed cells and PPP. Table 1 summarizes the results of these studies which were conduced with normal and sickled erythrocytes.

TABLE 1

| Sample | Force (Dynes) | Stress (Dynes/cm$^2$) | Deflection (mV) | Strain | E.M. (dynes/cm$^2$) |
|---|---|---|---|---|---|
| PPP | 4,900 | 509.3 | 74 | 0.0285 | 17,900 |
| PPP + P188 | 4,900 | 509.3 | 144 | 0.0554 | 9,200 |
| PPP + RBC | 4,900 | 509.3 | 39.4 | 0.0152 | 33,600 |
| PPP + RBC + P188 | 4,900 | 509.3 | 52.6 | 0.0203 | 25,150 |
| PPP + SRBC | 4,900 | 509.3 | 26.4 | 0.0102 | 50,100 |
| PPP + SRBC + P188 | 4,900 | 509.3 | 78.4 | 0.0302 | 16,900 |

where PPP is platelet poor plasma, P188 is Poloxamer 188, RBC is red blood cells, and SRBC is sickled RBC As can be seen from Table 1, normal erythrocytes, hematocrit=40%, increased the elastic modulus of PPP from 17,900 to 33,600 dynes/cm$^2$. When sickled erythrocytes were used, the elastic modulus increased to 50,100 dynes/cm$^2$. Addition of poloxamer 188, a copolymer with unique rheologic properties, to the sickled cell system prior to clotting reduced the elastic modulus to 16,900 dynes/cm$^2$. Similar, but much smaller, reductions occurred with normal red cells (33,600 dynes/cm$^2$ without poloxamer 188, and 25,150 dynes/cm$^2$ with poloxamer 188). Since poloxamer 188 is known to effect fibrin assembly, it is not surprising that effects were noted even in the absence of erythrocytes. In fact, the decrease in elastic modulus observed when poloxamer was combined with normal red blood cells might be entirely due to the effect of poloxamer 188 on fibrin structure.

FIGS. 8*a–c* show that there is a significant erythrocyte induced increase in clot elastic modulus. Comparison of the compression elastic modulus of clots formed from PPP with clots formed with PPP plus erythrocytes allows assessment of "excess"0 elastic modulus due to erythrocytes. Table 1 shows monitoring the compression elastic modulus allows altered erythrocyte deformability of SS cells to be detected. Specifically, a higher elastic modulus is detected for sickled cells than for normal cells. Table 1 also shows the potentially therapeutic effect of the rheologic agent poloxamer 188. Specifically, a tremendous decrease in elastic modulus is observed with poloxamer 188 is added to sickled cells, and this decrease can be attributed to an increase in erythrocyte flexibility. From FIGS. 8*a–c* and Table 1, it can be seen that monitoring the compression elastic modulus of a blood sample can provide valuable insight into the flexibility of erythrocytes and the effect of certain agents on erythrocyte flexibility.

While the invention has been described in terms of its preferred embodiments, those skilled in the art will recognize that the invention can be practiced with modification within the spirit and scope of the appended claims.

I claim:

1. An instrument for measuring clot elastic modulus and clot retraction force, comprising:
   - a pair of spaced apart plates;
   - a displacement sensor connected to at least one of said pair of spaced apart plates; and means for cyclicly compressing a blood sample between said spaced apart plates.

2. An instrument as recited in claim 1 wherein said means for cyclicly compressing includes a means for displacing a first plate of said pair of spaced apart plates towards a second plate of said pair of spaced apart plates.

3. A method for analyzing blood and plasma samples, comprising the steps of:

positioning a blood sample between a pair of spaced apart plates;

compressing, in a cyclical fashion with respect to time, said blood sample between said pair of spaced apart plates while said blood sample is clotting; and determining a clot retraction force and a clot elastic modulus for said blood sample with respect to time.

4. A method for analyzing blood and plasma samples, comprising the steps of:

providing a blood sample with a clot dissolving or clot destroying agent;

positioning said blood sample between a pair of spaced apart plates;

allowing said blood sample to clot;

compressing said blood sample between said pair of spaced apart plates during clotting;

identifying a compression elastic modulus for said blood sample; and relating said compression elastic modulus to erythrocyte flexibility.

5. A method as recited in claim 4 wherein said step of compressing is performed by displaying a first plate of said pair of spaced apart plates towards a second plate of said pair of spaced apart plates.

6. A method for analyzing blood and plasma samples, comprising the steps of:

providing a blood sample with a clot dissolving or clot destroying agent;

positioning said blood sample between a pair of spaced apart plates;

allowing said blood sample to clot and to dissolve;

compressing said blood sample between said pair of spaced apart plates in a cyclical fashion with respect to time while said blood sample is clotting and dissolving; and identifying a dissolution time for a clot formed from said blood sample.

7. A method as recited in claim 6, wherein said step of identifying includes the step of analyzing a clot retraction force for said blood sample with respect to time.

8. A method as recited in claim 6, wherein said step of identifying includes the step of analyzing an elastic modulus of said blood sample with respect to time.

9. A method as recited in claim 6, further comprising the step of providing said blood sample with a clotting agent.

10. A method for analyzing blood and plasma samples, comprising the steps of:

providing a blood sample with a clot dissolving or clot destroying agent;

positioning said blood sample between a pair of spaced apart plates;

allowing said blood sample to clot;

compressing said blood sample between said pair of spaced apart plates during clotting by displacing a first plate of said pair of spaced apart plates toward a second plate of said pair of spaced apart plates wherein said step of compressing is performed cyclically with respect to time;

identifying a compression elastic modulus for said blood sample; and relating said compression elastic modulus to erythrocyte flexibility.

* * * * *